United States Patent [19]

Magnussen, Jr. et al.

[11] Patent Number: 5,214,593
[45] Date of Patent: May 25, 1993

[54] METHOD AND APPARATUS FOR EXTENDING THE LINEAR DYNAMIC RANGE OF ABSORBANCE DETECTORS INCLUDING MULTI-LIGHTPATH FLOW CELLS

[75] Inventors: Haakon T. Magnussen, Jr., Orinda; Roy P. Moeller, Hayward, both of Calif.

[73] Assignee: Rainin Instrument Co., Inc., Emeryville, Calif.

[21] Appl. No.: 610,416

[22] Filed: Nov. 7, 1990

[51] Int. Cl.$^5$ .................. G01N 21/01; G01J 3/42
[52] U.S. Cl. .................. 364/497; 364/571.02; 356/436
[58] Field of Search .......... 364/497, 498, 573, 571.01, 364/571.02, 413.07, 413.08, 509; 356/319, 320, 436

[56] References Cited

U.S. PATENT DOCUMENTS

| | | | |
|---|---|---|---|
| 4,348,115 | 9/1982 | Walker et al. | 356/436 |
| 4,581,714 | 4/1986 | Reid | 364/573 |
| 4,587,624 | 5/1986 | Banno | 364/497 |
| 4,815,847 | 3/1989 | Oberheim et al. | 356/319 |
| 4,848,904 | 7/1989 | Sapp et al. | 356/319 |
| 4,935,875 | 6/1990 | Shah et al. | 364/497 |

OTHER PUBLICATIONS

Goraczko, A. et al., "The Universal Analytical–Preparative Flow Cell", Journal of High Resolution Chromatography & Chromatography Communications, vol. 9, p. 255 (Apr. 1986).

Primary Examiner—Parshotam S. Lall
Assistant Examiner—Michael Zanelli
Attorney, Agent, or Firm—Robert R. Meads

[57] ABSTRACT

A method and accompanying apparatus for automatically extending the linear dynamic absorbance range of absorbance detectors including multi-lightpath flow cells. The absorbance of a reference beam in a relatively short reference path is multiplied by a ratio of the absorbance of a sample beam in a relatively long sample path to the reference path absorbance in developing a relative absorbance for the sample path beyond its linear dynamic range.

18 Claims, 12 Drawing Sheets

METHOD AND APPARATUS FOR EXTENDING THE LINEAR DYNAMIC RANGE OF ABSORBANCE DETECTORS INCLUDING MULTI-LIGHTPATH FLOW CELLS

BACKGROUND OF INVENTION

The present invention relates to absorbance detectors such as those commonly used in high performance liquid chromatography (HPLC), and, more particularly, to a novel method and accompanying apparatus for automatically extending the linear dynamic range of such detectors.

The definition of absorbance is:

$$A = \epsilon c l$$

where:
- $A$ = the absorbance in absorbance units (AU),
- $\epsilon$ = the molar extinction coefficient of the sample or the molar absorptivity,
- $C$ = the sample concentration in moles/liter, and
- $l$ = the pathlength of the measurement cell in cm.

In an ideal absorbance detector the indicated absorbance is a linear function of sample concentration and Beer's Law is followed. That is:

$$A = \log(I_o/I) \text{ (Beer's Law)}$$

and:

$$I_o/I = 1/T \text{ (Definition of transmittance)}$$

where:
- $I$ = the transmitted light intensity
- $I_o$ = the incident light intensity
- = the transmittance In an actual absorbance detector Beer's Law breaks down at higher absorbances and nonlinearities occur. There are a number of reasons for such nonlinearities aside from the chemistry of the sample. Some of the more common reasons are outlined below:

Stray Light

Light at wavelengths removed from a selected wavelength is absorbed at a different rate by a sample than light at the selected wavelength because $\epsilon$ is a function of wavelength. Stray light can be caused by overlapping orders from a grating in the associated system monochromator or by light at other wavelengths that is scattered inside the instrument and get through the flow cell to the photodetector. Stray light can cause a detected background signal which is not absorbed by the sample at the same rate as the selected wavelength. Such a background will cause a distortion to Beer's Law.

The finite bandwidth of the monochromator also is sufficient to cause nonlinearities even if stray light does not exist at wavelengths far removed from the selected wavelength. Bandwidths are typically 5 to 10 nm in HPLC Absorbance detector. The molar extinction coefficient of most compounds, at certain wavelengths, can easily vary over a 5 to 10 nm wavelength range by amounts sufficient to cause non Beer's Law behavior. Instrument bandwidth limits linear response to less than 2 AU in most HPLC absorbance detectors.

Electronics Errors

At high absorbances the detected photo signal through the sample flow cell become very small. Direct Current offset errors in the electronics associated with an absorbance detector can be significant and have the same effect as stray light in causing non Beer's Law behavior. Instead of a very high absorbance signal approaching a zero value (corresponding to infinite absorbance) it approaches the zero offset error. This causes the signal to approach an absorbance value other than infinity for very high absorbances. For example, if a signal corresponding to zero absorbance equals 1 volt at the output of an amplifier and a zero offset error of 1 mv exists, the absorbance values above 3 AU cannot exceed a reading of 3.0 AU (i.e., a true signal of 2 AU would indicate 1.96 AU and a 3.0 AU signal would indicate 2.7 AU etc). Also the linearity and accuracy of other electronic components such as the log conversion circuitry can effect absorbance accuracy.

Only the very finest spectrophotometers, with bandwidths less than 1 nm can achieve good linearity to 3 AU. However, with such small bandwidths detected light levels at zero absorbance are quite low and hence noise levels are high. Sensitivity to small absorbance signals are limited to changes which are considered too large for practical HPLC detection. In order to get sufficient light levels through a small HPLC flow cell to achieve low noise operation bandwidths on the order of 5 to 10 nm are required. This inherently limits linear range to less than 2 AU for most chemical compounds.

Samples at high concentrations can produce absorbance values beyond the linear range of a given flow cell pathlength. Traditionally, chemists have had to change flow cells to ones with shorter pathlengths to detect higher concentrations. For small absorbance signals pathlengths on the order of 5 to 15 mm are used (typically 8 to 10 mm). For high sample concentrations with large absorbance signals exceeding 1 AU and going to 10 AU or higher (in a 10 mm pathlength) pathlengths less than 2 mm are typically used in order to scale the absorbance into the linear range of the instrument. Normally a user selects a flow cell and installs it into his detector depending on what type of work he is going to do. A flow cell with two pathlengths built into the same structure is described by Goraczko, (A. Goraczko and D. Janota, *The Universal Analytical-Preparative Flow Cell*, Journal of High Resolution Chromatography & Chromatography Communications, Vol 9, April 1986, pages 255-256.) where the user only has to turn a knob to rotate the flow cell 90 degrees to change pathlengths. In either case an instrument has a linear dynamic range limited from the noise level to the maximum linear AU response. A typical HPLC absorbance detector has a linear dynamic range of about 100,000:1 (20 μAU to 2 AU).

Accordingly, there is a continuing need for absorbance detectors having expanded linear dynamic ranges and which do not require the mechanical changing of flow cells for use with high concentration samples. The present invention satisfies such needs by providing a method and apparatus for automatically extending the linear dynamic range of absorbance detectors including multi-lightpath flow cells. Preferably, the method and apparatus of the present invention are as embodied in the DYNAMAX Model UV-1 HPLC absorbance detector soon to be released by the Rainin Instrument Co., Inc., the assignee of the present invention.

SUMMARY OF INVENTION

Basically, the improvement provided by the present invention is a method and associated apparatus for extending the linear dynamic range of an absorbance detector including a multiple light path flow cell having at least a relatively long sample beam passageway and a relatively short reference beam passageway, each passing the sample fluid under test and including photo detector means for receiving the sample and reference beams and for developing output signals which are measures of the absorbance of the sample and reference beams in the sample fluid. The method comprises the steps of and includes apparatus for (1) determining the absorbance (A1) of the sample beam in passing through the fluid sample in the sample passageway for fluid absorbances within the linear dynamic absorbance range of the sample beam passing through the sample passageway.

(2) determining the absorbances (A2 and A2') of the reference beam in passing through the fluid sample in the reference passageway for fluid sample absorbances respectively within and beyond the linear dynamic absorbance range of the sample beam passing through the sample passageway, and (3) from $A_2'$ developing a linearized relative absorbance ($A_1'$) for the sample beam passing through the sample passageway over fluid absorbances beyond the linear dynamic absorbance range of the sample beam passing through the sample passageway.

Preferably, the developing of the linearized relative absorbance ($A_1'$) comprises multiplying $A_2'$ by the ratio of $A_1$ to $A_2$ or a ratio of a difference ($A_D$) between $A_1$ and $A_2$ to $A_2$, e.g. $A_D/A_2$.

BRIEF DESCRIPTION OF DRAWINGS

FIG. 6a illustrates a logratiometer analog to digital converter useful in the present invention while FIG. 6b is a timing diagram for the circuit of FIG. 6a.

DETAILED DESCRIPTION OF INVENTION

Figure 1:
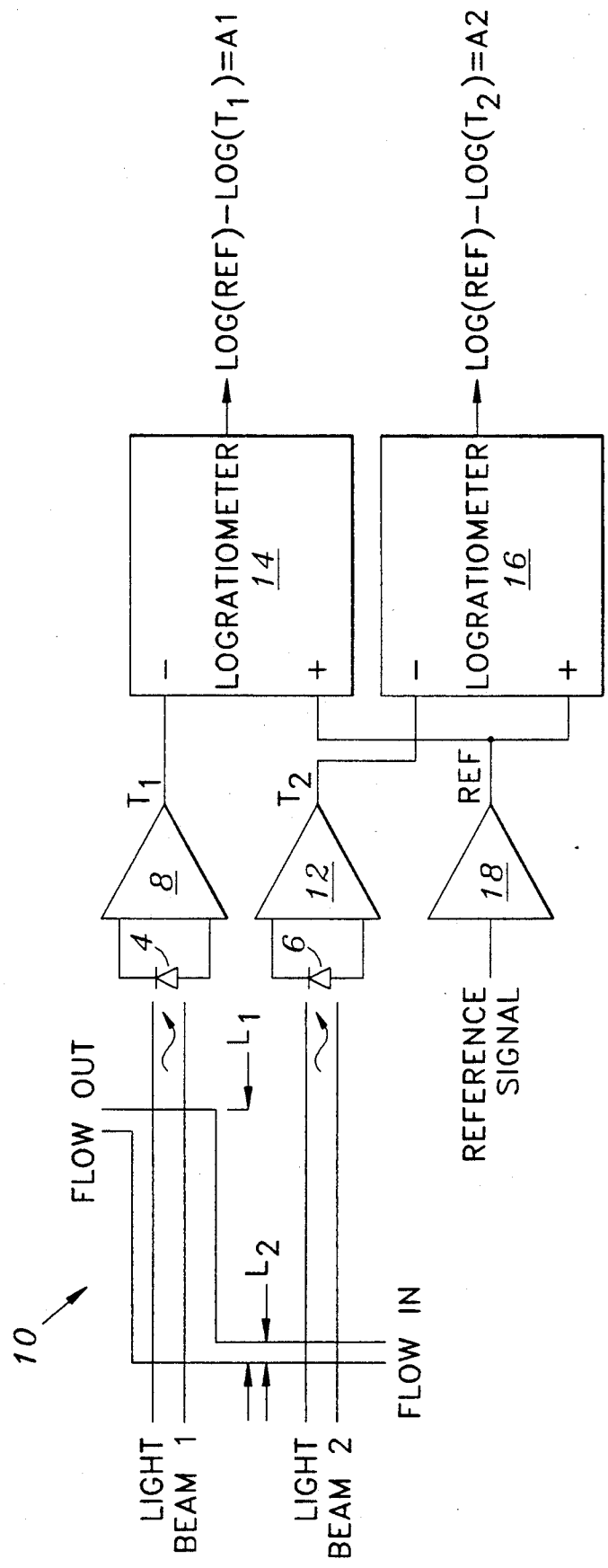
FIG. 1 and FIG. 2 are block diagrams of hardware methods of calculation absorbance from two different pathlengths.
Figure 2:
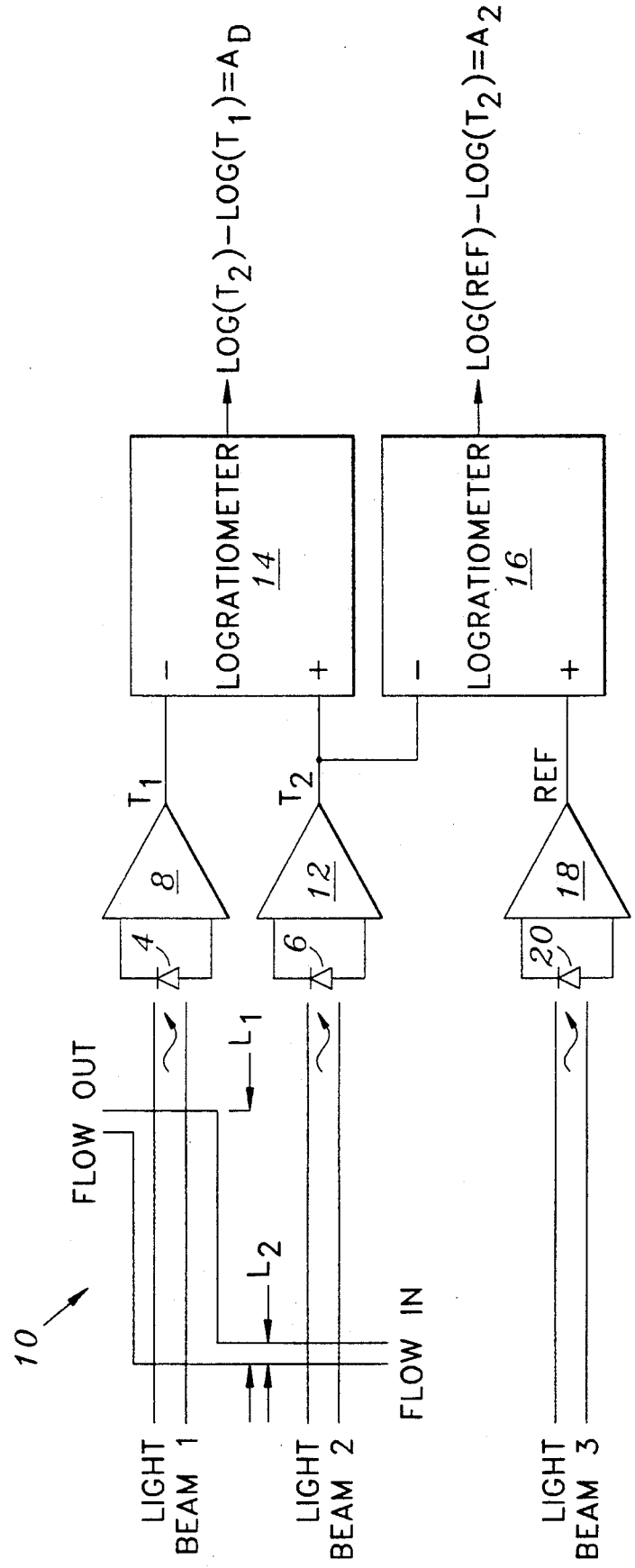

FIGS. 1 and 2 illustrate block diagrams of hardware methods where absorbance is calculated from two different pathlengths simultaneously. A flow cell (10) with two different optical pathlengths is illustrated. Light beam 2 is shown passing through a short pathlength, $L_2$, and light beam 1 is shown passing through a longer pathlength, $L_1$. Flow of the sample through the flow cell can be in either direction but is illustrated as going through the short path first and then exiting from the long path. [Ideally, both pathlengths would be in the same physical space, but construction of such a cell and associated optics is complex.] For simplicity, the two flow cells are shown as being separate and connected in series. The connecting volume between the two cells is kept very small to minimize the effects of the separation volume between the two pathlengths. The light beams (1 and 2) are directed to a pair of photodetectors (diodes) 4 and 6 respectively and the resulting signals are amplified by a pair of amplifiers (8 and 12) with outputs which represent the optical flux through each pathlength of the flow cell ($T_1$ and $T_2$).

Figure 3:
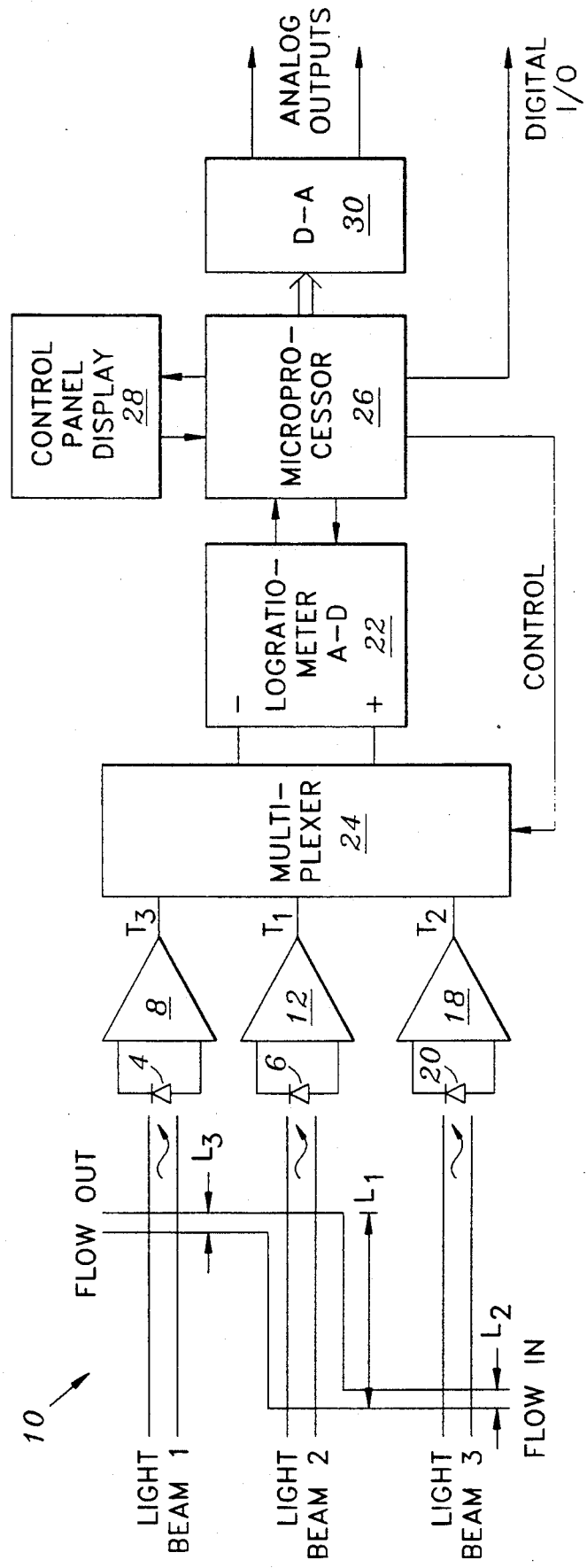
FIG. 3 is an alternate configuration including a single logratiometer.

In FIG. 1 a logratiometer (14) outputs the absorbance in the long pathlength, $L_1$, and a logratiometer (16) calculates the absorbance in the short pathlength, $L_2$, by comparing them to a reference signal. Ideally the reference signal (REF output from amplifier 18) is from a third detected light beam through a third pathlength, $L_3$, or just air as shown in FIGS. 2 and 3. However, for reduced hardware complexity and cost it can also be from a fixed reference voltage at the expense of increased noise on the calculated absorbances.

In FIG. 2 the logratiometer (14) outputs the absorbance in beam 1 minus the absorbance in beam 2. Since the absorbance is proportional to pathlength, the output represents the equivalent absorbance in a pathlength of $L_1-L_2$. This method has the advantage of providing true dual beam performance on the path difference signal without the need for a third optics beam (the third optic beam in FIG. 2 is optional and is only necessary to provide true dual beam operation for the short pathlength).

FIG. 3 shows an alternate configuration which only requires one logratiometer (22) wherein the three inputs ($T_1$, $T_2$, and $T_3$) are multiplexed by a conventional multiplexer (24) at a sufficiently high rate between the different configurations so that the different outputs are essentially acquired simultaneously. If a microprocessor (26) is used, the logratiometers could be effected in the software. However, since an analog to digital converter is required in either case it is convenient to have the A-D (22) itself take the log of the signals while converting to the digital domain for processing in the microprocessor (26), display by a control panel display (28) and subsequent digital to analog conversion by a D-A converter (30).

Figure 4:
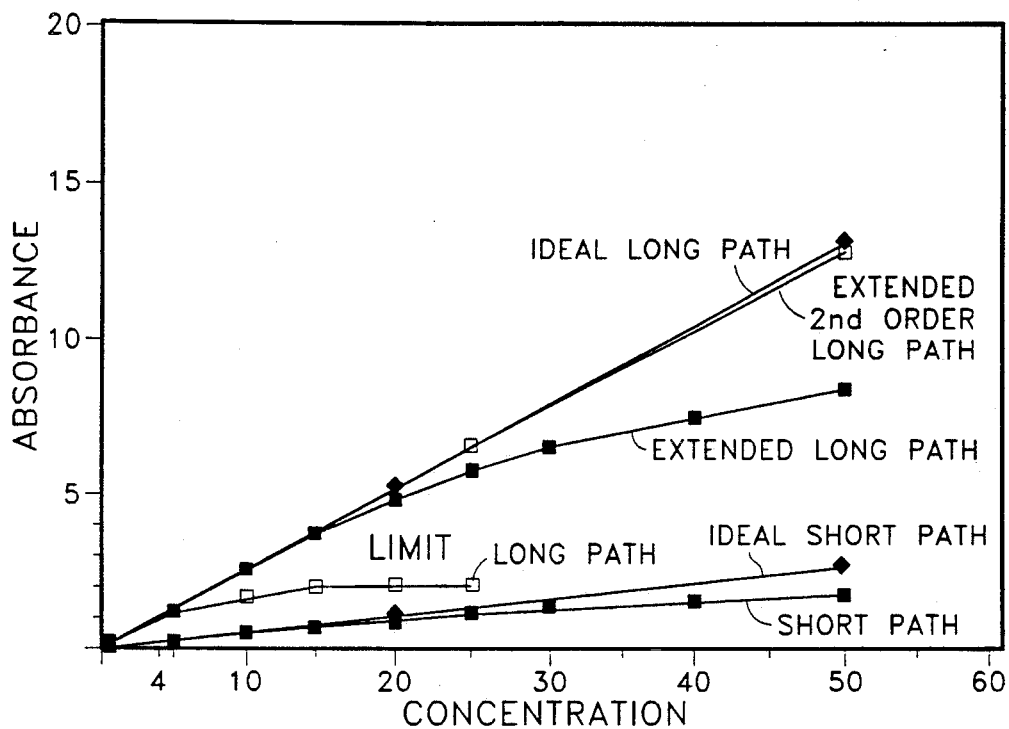
FIG. 4 graphically illustrates a hypothetical response of the systems shown in FIGS. 1, 2 and 3 to a compound at different concentrations.

FIG. 4 graphically illustrates a hypothetical response of the systems shown in FIGS. 1, 2 and 3 to a compound at different concentrations. The "Long path" curve shows the long path or the path difference absorbance and the "Short Path" curve shows the absorbance from the short path. For the purpose of illustration, the ratio between the two responses as shown is approximately 5 (that is, the long path or path difference is about 5 times as long as the short path). In both cases noticeable non linearities are exhibited when compared to the extended "Ideal Response" lines above a response of about 1 AU, which corresponds to a concentration of $4_r$ for the long response and a concentration of 20 for the short path.

Just having two different absorbance responses available simultaneously would be convenient to a user. The user could select which response he wanted to monitor. However, a far more useful configuration for the user would be to have an instrument which automatically combines the two different response signals into one coherent signal which effectively extends the useful linear dynamic range of the long path response.

In its simplest form, such an extended range instrument would calculate the ratio between the two responses when both signals were linear and then multiply the short path response by the ratio (ratio value of 5 below a sample concentration of 4 as illustrated in FIG. 4). One continuous absorbance output then is generated from the two signals and represents the long pathlength at lower concentrations and changes over to the short path absorbance multiplied by the response ratio for higher absorbances when the long pathlength starts going nonlinear.

As illustrated in FIG. 4, the "Extended" output which represents the combination of the two absorbance signals is linear to a concentration of 20 and produces a linear response to about 5 AU relative to the long path instead of only 1 AU. The linear dynamic range of the L instrument is extended by a factor of 5 in this example. The user automatically gets the benefit of the high sensitivity (low noise) of the long pathlength for small sample concentrations and simultaneously gets the linear response to high sample concentrations from the short pathlength without having to change flow cells or switch ranges. A ratio of long pathlength to short pathlength of 10 would extend the linear dynamic range of an instrument by a factor of 10 by this simple technique. A typical HPLC detector with a pathlength ratio of 10 using this technique would have a linear dynamic range of about 1 million to 1.

The extended signal looks to the user just as if the long pathlength had a fantastically large range. The short pathlength signal is simply scaled up to match the response factor of the long pathlength; therefore, the actual output is a relative absorbance rather than an absolute absorbance.

Extending the linear range by this technique allows for two benefits. The first benefit is that the user does not have to change flow cells as often. The second benefit of this technique is that it can be used to the improve the light throughput of the optics by relaxing the requirement for narrow bandwidths. More light throughput allows the signal to noise ratio to be increased for small absorbance signals thus improving sensitivity for small absorbance changes. Since the linear range is extended for a given bandwidth, the bandwidth can be increased, allowing more light through the optics, and still allow the instrument to have a larger linear range than it would with a smaller bandwidth not using the extended range technique.

In general, when both absorbance signal are linear in FIG. 2 then:

$$A_D/A_2 = (\epsilon c l_1 - \epsilon c l_2)/\epsilon c l_2 = (l_1 - l_2)/l_2 = K_o$$

$A_D$ is generated from the pathlength difference between the long path and the short path rather than just the long pathlength. This is preferred because it gives lower noise operation and it does not require a third optic beam for low noise operation on the long pathlength. Generally the longer path absorbance signal will deviate from Beer's Law first while the shorter path signal remains linear.

When the longer path absorbance deviates from linear response the calculated absorbance ratio is no longer a constant but varies with concentration. That is:

$$K_A = A_D/A_2$$

If $K_A$ is memorized in a table, as the concentration increases in the flow cell for each chromatographic peak, $K_A$ can be used to further extend the linear dynamic range beyond the simple, first order, implementation of extended range. This of course assumes that the nonlinearities in the short pathlength track those in the long pathlength for equivalent absorbances for a given peak. In other words, while the short path signal is still linear the nonlinear nature of the long pathlength is studied and the resulting nonlinearity characteristic is used to correct the extension of the short path when it begins to experience nonlinearities. In the example illustrated in FIG. 4 the nonlinear nature of the long pathlength above a concentration of 4 is tracked and memorized. When the concentration exceeds 20 these memorized response ratios ($K_A$) are used to extend the short pathlength instead of $K_o$. The value of $K_A$ measured when $A_D$ is equal to 7 is used to extend $A_2$ when it is also equal to 7 and the value of $K_A$ measured at $A_D$ equal to 10 is used to extend $A_2$ when it equals 10 and so on.

In general:

$$\textit{Ideal Extended Response (long path)} = K_o^2 * A_2/K_A$$

This second order correction on the response of the extended range output theoretically extends the linear dynamic range by another factor of $K_o$ such that for a path ratio of 10, the linear dynamic range could be extended by factor of 100, provided that $A_D$ continues to respond. In actual practice $A_D$ saturates at some point and no longer responds to any further increase in absorbance in the long path since the detected signal becomes so small. Nevertheless, using this second order correction technique can accurately linearize the extended range response beyond $K_o$ times the maximum value expected for $A_D$. For example, the trace labelled "Extended 2nd order" in FIG. 4 is linear to a concentration well above 50 units corresponding to a relative absorbance above 12.5 AU.

In order to effectively use the second order correction for extended range, the values for $K_A$ must be determined accurately in a short period of time. Accurate determination of the response ratios requires that both signals have a high signal to noise ratio. Normally the requirement for a high signal to noise ratio rules out single beam operation on the short pathlength unless a low noise lamp is used. Best results are obtained if a third optic beam is used as the reference signal for the short pathlength as shown in FIGS. 2 and 3.

If the short pathlength is separated by a finite volume from the long pathlength, as illustrated in FIGS. 1 and 2, then an error will occur due to the change in absorbance as a function of volume flowed. For a given $d(AU)/dV$, the flow cell volume must be kept small enough to assure that the resultant errors are acceptable or appropriate corrections must be made. Additionally, if the flow cell volumes are not evenly swept along their entire pathlengths, additional short term errors will occur on $K_A$. For these reasons a system which successfully applies the second order correction to the extended range basically must include a third light beam with a third pathlength as shown in FIG. 3 to apply appropriate corrections to $K_A$ unless the two pathlengths occupy the same volume not allowing for any separation volume between the two pathlengths.

Detailed implementation of the first order extended range will be described before a method to use the second order extended range is described.

Dual Beam Implementation of First Order Extended Range

Instantaneous (not averaged) calculated values of $K_o$ using measured absorbance values in the linear range of both absorbances can be quite different than the actual ratio of pathlengths due to various sources of error as mentioned above for $K_A$. Single beam operation on the short pathlength with a relatively noisy lamp will cause the instantaneous value of $K_o$ to be noisy (single beam operation on the short path implies that only two beams are used in the system and a fixed voltage reference is used for the short pathlength as shown in FIG. 1). Also the finite separation volume between the two different pathlengths together with the change in absorbance as a function of volume causes the calculated $K_o$ to be different on different portions of a chromatographic peak. Despite these and other sources of error the first order extended range technique can still be used provided care is taken in calculating $K_o$ and the other constants required to properly extend the short path absorbance signal relative to the long path absorbance. For example, $K_o$ should be determined by filtering data over sufficient time or by averaging data over a sufficient number of chromatographic peaks to guarantee that a stable, accurate value that represents the true ratio of flow cell pathlengths can be calculated.

When, as in the DYNAMAX UV-1, a Xe flash lamp is used as a light source and it is flashed at a 60 Hz rate, the system illustrated in FIG. 3 can be multiplexed between two monitoring configurations at a 30 Hz rate. If the third beam and pathlength in FIG. 3 is replaced by a fixed voltage reference then single beam operation on the short path will result. A typical "low noise" Xe flash lamp may have 2% flash to flash amplitude variations. In the path difference configuration (FIGS. 2 and 3) the instrument still behaves as a dual beam device and the lamp amplitude variations are common mode to both the signals so that when the logratio of both signals is determined the lamp amplitude variations cancel out and do not effect the resulting absorbance signal. In the short pathlength configuration (FIG. 1) the reference signal is a fixed voltage so the lamp amplitude variations effect the absorbance signal directly. A 2% peak to peak lamp white noise at a 30 Hz rate translates to an absorbance noise of $1.4 \times 10^{-3}$ AU peak to peak when filtered by a 0.4 second time constant. The short pathlength signal is multiplied by $K_o$ when it is extended to a relative absorbance equivalent to a theoretical absorbance determined from a path difference measurement; therefore, its noise is also multiplied by $K_o$. If $K_o$ is approximately 8 then the resulting noise for the extended short pathlength absorbance will be on the order of $1 \times 10^{-2}$ AU peak to peak when filtered by a 0.4 second time constant as compared to a noise of about $2 \times 10^{-5}$ AU peak to peak for the path difference absorbance signal. Although the relative absorbance from the single beam determination of the short pathlength signal is about 500 times noisier than the dual beam determination from the longer path difference signals, it nevertheless is a useful signal.

The path difference absorbance signal is typically linear to well over 1 AU so that an instrument with an extended range feature does not have to use the noisier short path signal until typically absorbances above 1 AU are indicated. At relative absorbance levels larger than 1 AU, the noise on the signal will typically be less than 1% when filtered by time constants above 0.4 seconds. Noise levels of this magnitude will allow chromatographic peak heights to be determined to better than 1% accuracy. Peak areas can be determined much more accurately since the noise is integrated over the width of the peak. The ability of an instrument to indicate relative absorbance to 10 AU and above would be very useful to chromatographers working with concentrated or large samples such as in preparative or semi-preparative liquid chromatography applications.

Reproducibility from chromatography to chromatography is an important requirement for chromatographers. Generally individual components within an LC system should not contribute more than 0.1% variability from run to run. With this in mind, $K_o$ should be stable to within 0.1% day in and day out for normal operation of the absorbance detector. There are three ways this can be done: 1.) $K_o$ can be predetermined for a given flow cell when it is constructed and this value can be manually entered into the detector by the user when the flow cell is installed in the detector. 2.) $K_o$ can be encoded on individual flow cells and automatically read as a constant by the detector. Or, 3.) $K_o$ can be automatically calculated by a detector by using the response from the two different pathlengths. The first two methods listed above guarantee stability of $K_o$, however, both methods require careful determination of $K_o$ when the flow cell is fabricated which increases the manufacturing cost. In addition, the first method requires the user to enter this value into the instrument which may not always be done correctly. The second method, although more reliable than the first, has the additional cost of an encoder. The third method is the lowest cost, the most convenient for the user, and theoretically, with the proper algorithm, the most accurate.

Besides stability, $K_o$ must also be accurate. $K_o$ should be accurate to within 1% of its actual value. The short path typically has a pathlength of 0.5 to 1 mm. A 1% variation in this pathlength is equivalent to 0.005 to 0.01 mm. If a flow cell is taken apart to be rebuilt or cleaned by the user, it is possible that the spacing between the windows on the short path will change by more than 1% when the flow cell is reassembled. Such an operation would require that $K_o$ be determined again; this would require that the flow cell be sent back to the factory for such operations if methods 1 or 2 were used. Only automatic determination of $K_o$ by the detector (method 3) would guarantee that $K_o$ is determined accurately enough after a user disassembles and reassembles a flow cell.

In order to automatically determine $K_o$ with a long term stability of 0.1% and an accuracy of 1% certain requirements exist when a Xe lamp, with a worst case noise of 5% peak to peak, and a flow cell with a delay volume on the order of 10 to 20 μl between the pathlengths are used. $K_o$ must be averaged over a large number of points to reduce the noise and average the derivative errors. $A_D$ and $A_2$ are used to determine $K_o$ only when both signals are in their linear range. Consistent errors on either signal will be transferred to $K_o$.

Therefore, it is important that both absorbance signals be accurate to within 1% and reproducible to within 0.1% when calculating $K_o$.

$A_D$ and $A_2$ are both defined to have zero absorbance at the same point in time when a user presses an auto zero button of the DYNAMAX UV-1 during baseline determination of a chromatogram as described hereinafter. The corresponding zero offsets both must be accurate to within 0.1% in order to assure that new calculated values for $K_o$ will be within 0.1% of the calculated values before auto zero was last pressed by the user. Since the noise on $A_D$ is so low, only one data point is required to determine its offset. However, because the noise on $A_2$ is large, its zero offset must be averaged over a large number of points in order to guarantee 0.1% precision in extended range.

Figure 5:
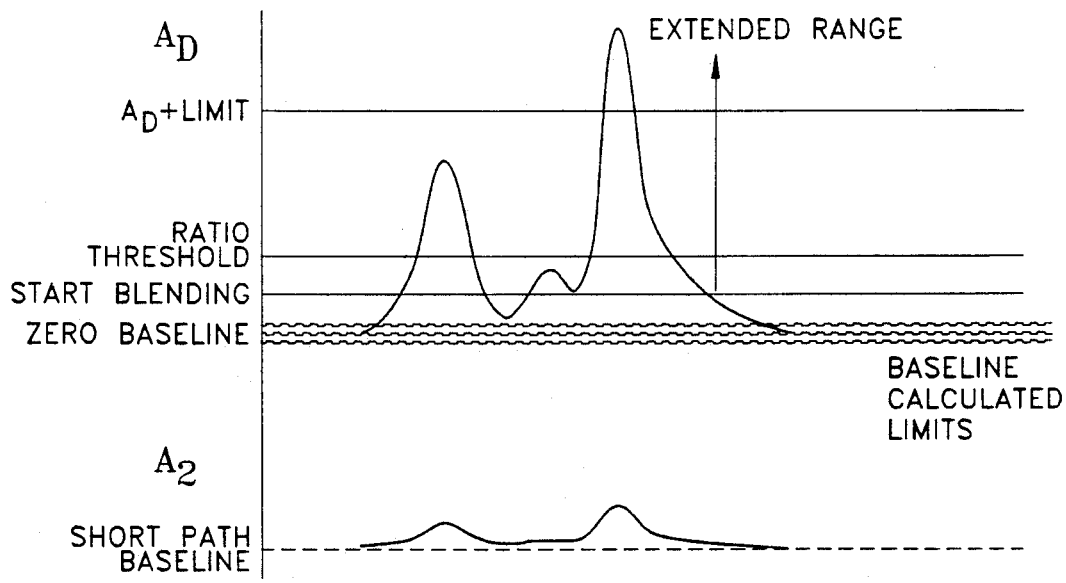
FIG. 5 illustrates a typical chromatogram with the absorbance signals $A_D$, $A_2$ and extended $A_2$ superimposed on $A_D$.

FIG. 5 illustrates a typical chromatogram with the absorbance signals $A_D$, $A_2$ and the extended $D_2$ superimposed on $A_D$. The response of $A_2$ is one eighth that of $A_D$ so that $K_o$ is equal to 8. $A_D$ will not respond above its +limit because it clips at this point. When extended range is activated, at some point before the +limit (for example: 10% of +limit) the relative absorbance, calculated from $A_2$, is blended with $A_D$. Thus, as the relative absorbance increases, the contribution from $A_D$ is decreased in the blend until it makes no contribution when the +limit is reached. Above +limit the extended range output is solely determined from extending $A_2$. The signals are blended over a finite region in order to minimize sudden discontinuities in the output due to absorbance derivative errors or small errors in the measured constants.

Logratiometer Analog to Digital Converter

As mentioned earlier, since an A-D converter, 22 in FIG. 3, is required to input photometeric measurements to the microprocessor (26) it is convenient to have the same A-D take the logratio of the light intensity measurements. A method that has been found to be convenient with the use of a Xe flash lamp flashing at rates up to 120 Hz is illustrated in FIG. 6a with its corresponding timing diagrams illustrated in FIG. 6b.

Figure 6A:
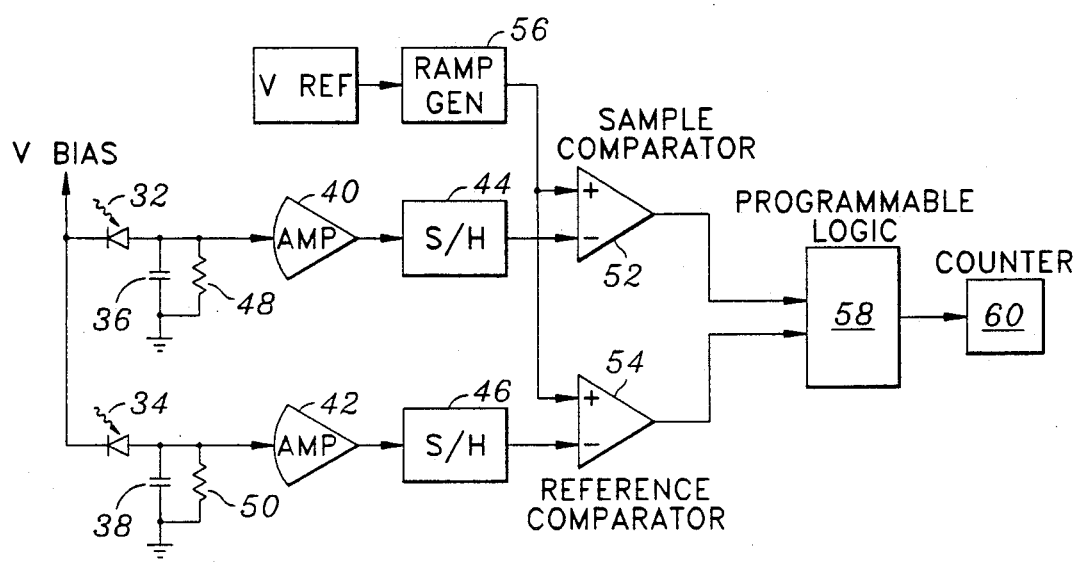

Referring to FIG. 6a, sample and reference photodiodes (32 and 34) are reversed biased by V-BIAS to improve their response and recovery without resulting in saturation or non linearities to light pulses from the Xe flash light source. The high speed current pulses (1 to 2 μs widths) are integrated by the attached capacitors (36 and 38). The resulting voltage across each capacitor is amplified by an amplifier (40, 42) and AC coupled into the sample and hold circuit (44, 46) for each channel. AC coupling essentially eliminates any effects from DC leakage currents, dark currents, offset currents or voltages in the amplifiers or photodiodes. Resistors (48 and 50) across each capacitor (36 and 38) essentially discharge the capacitors to zero before the next current pulse arrives. The voltage at the output of each sample and hold represents the integrated light flux in the pulse striking each photodiode with minimal carry over from the previous flash. Low carry over from the previous flash allows the detector to have an extremely fast response time and low sensitivity to lamp noise. Fast response time allows good performance in multiwavelength applications where wavelength is rapidly multiplexed.

The output from each sample and hold circuit goes into a comparator (52,54). The reference input to each comparator is connected to the output of a exponential ramp generator (56 powered from V REF). The outputs of each comparator connects to logic (58) which produces a gate signal to gate a high speed counter (60) on and off to generate a digital count which is proportional to the difference of the log of the reference signal and the log of the sample signal.

Figure 6B:
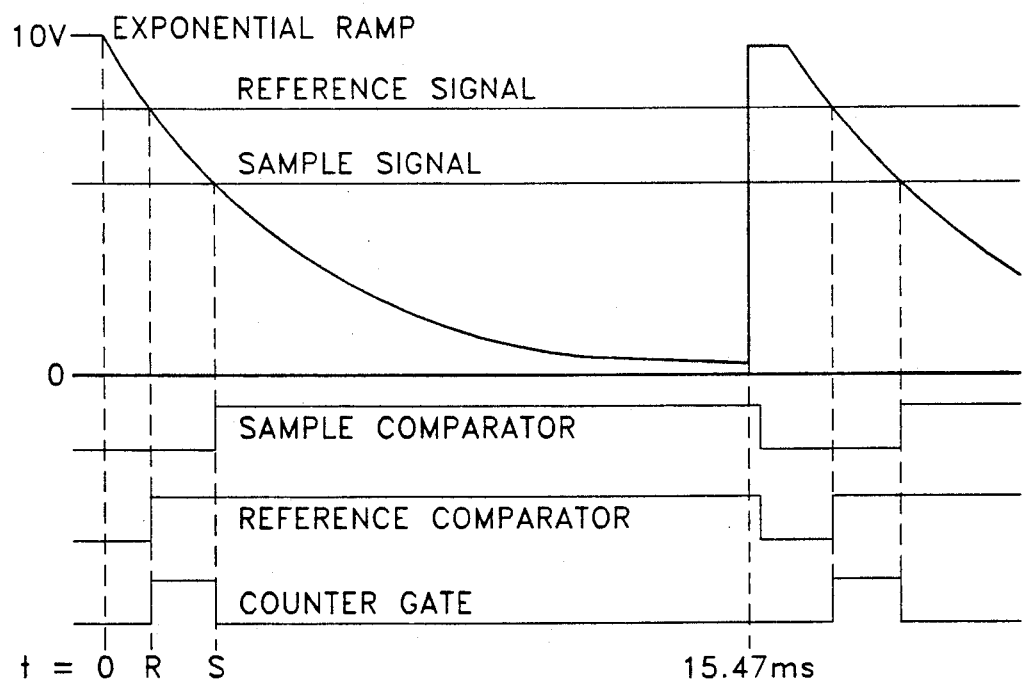

FIG. 6b illustrates the timing of these signals. The exponential ramp starts at zero time (t=0 ms) at a high voltage (i.e.; 10 volts) and exponentially decays to a low voltage (about 60 mV) near the end of a period (t=15.47 ms, leaving a 1.2 ms overhead with a 60 Hz conversion rate). The reference and sample signals are compared to this ramp by separate comparators. Each comparator (52, 54) changes its output state when the ramp passes below the signal level as indicated on the timing diagram. The programmable logic block (58) produces the gate signal as indicated on the timing diagram as well as determines the sign bit depending on which signal is larger. At t=0 the counter (60) is reset to zero count. The gate signal allows the counter to count high speed clock pulses between the times t=R and t=S. The resulting count is proportional to the logratio of the reference signal to the sample signal (i.e.; log reference − log sample).

The counter counts a 29.376 MHz clock so that a maximum count of 454,447 counts can be accumulated in a 15.47 ms period corresponding to about 2.22 AU (10 Volts to 60 mV). This produces a resolution of about 5 μAU per count at a 60 Hz rate which is much smaller than the lowest shot noise expected from the system at this bandwidth.

The microprocessor (26 in FIG. 3) inputs and processes the counter data and sign bit for each period with appropriate offsets and scaling factor when calculating absorbance as well as absorbance limits. The counter's +limit is determined by the amplitude of the reference signal and is equal to the maximum count (454,447) minus the equivalent count between t=0 and R. Likewise, the counter's −limit is equal to the count between t=0 and R. From the counter's +, −limits the +, −AU limits can be determined when the zero AU value is taken into account. A user defines zero AU when he presses the Auto Zero button on the control panel of the DYNAMAX UV-1. The counter count at zero AU becomes the zero offset value. The zero offset for a path difference signal would be the count S−R and the offset for the reference signal would be the count at R. The zero offset value is subtracted from the counter count when absorbance is calculated. Therefore, the +limit for absorbance count is the counter +limit minus the zero offset count. Absorbance counts and limit counts are scaled by the 5 μAU per count scaling factor before being outputed.

Baseline Determination

In order to guarantee 0.1% precision or variance in the zero offsets and in the determination of $K_o$ a number of conditions must be met. Since $A_2 = A_D/K_o$, the average acceptable peak to peak noise in determining the baseline of $A_2$ will be:

*Averaged Baseline*
*Noise(P—P)≦6\*Variance\*Threshold/$K_o$*

Where
    Variance=the rms precision required (i.e.; 0.1%), where rms is the root mean square which is approximately one-sixth of the peak to peak value.

Threshold = the absorbance of $A_D$ above which $K_o$ is calculated.

If the desired Averaged Baseline Noise is ratioed with the unfiltered noise on $A_2$, the ratio of improvement can be calculated as:

*Noise Ratio = Fast Noise/Averaged Baseline Noise*

Where:

Fast Noise = the noise on $A_2$ with no averaging

To achieve the desired Noise Ratio the minimum number of points that must be averaged is:

$$N \geq (Fast\ Noise * K_o/6 * Variance * Threshold)^2$$

Where:
N = number of data points that must be averaged to achieve the desired Variance.

For example: A Xe lamp with 5% peak to peak noise (0.02 AU P-P), a desired Variance of 0.1%, a $K_o$ of 8, and a Threshold of 0.5 AU will require $N \geq 2850$ points.

When a user presses the auto zero button in the DYNAMAX UV-1 in the above example, the instrument should theoretically average 2850 points of $A_2$ in order to determine the $A_2$ zero offset to sufficient accuracy. This obviously is not practical to do all at once without regard to changes in the baseline since 2850 points represents 95 seconds of data at 30 Hz. The baseline could easily change to values other than zero in this length of time. If one assumes that the baseline is steady for at least one second after auto zero is pressed, at least 30 points can be averaged without regard to changes. In addition, if $K_o$ is known to have an accurate value, additional points, after the initial 30, can also be averaged by correcting $A_2$ for changes in absorbance by subtracting the quantity $(A_D/K_o)$ from $A_2$ before it is averaged.

When $K_o$ is known to be accurate to within 1%, the baseline points can be corrected for and averaged as baseline points as long as $(A_D)$ is less than 0.3 AU (Baseline Calculate Limits shown on FIG. 5).

If the other errors are not negligible, the Baseline Calculate Limit should be decreased to something less than 0.3 AU. A baseline averaging routine based on the above method could be active all the time so that at anytime when $(A_D)$ is less than the Baseline Calculate Limit those points would be corrected and averaged. This would allow the baseline zero offset value for $A_2$ to be kept current with an average of thousands of points at 30 Hz while in the extended range mode. The routine could also be used even if the instrument were not in an extended range mode, provided the instrument switches to the short path configuration to determine $A_2$ occasionally, such as once per second (during non extended range operation, the instrument should spend most of its time reading the path difference signal in order to optimize the signal to noise ratio on $A_D$). If $K_o$ is not known to be accurate, the baseline limit should be reduced to 0.01 AU so as not to introduce excessive errors in the averaged $A_2$ zero offset due to an improper $K_o$.

Determination of $K_o$

In determining the effects of noise on the variance of $K_o$ a similar analysis as above can be done. First it is assumed that the noise on $A_D$ is not a factor so that the noise on $K_o$ is totally due to noise from $A_2$.

$K_o$ Noise Ratio = Fast Noise * $K_o$/6 * Variance * $A_D$

Therefore the number of points that be sampled is $$N \geq (Fast\ Noise * K_o/6 * Variance * A_D)^2$$

Notice that N is proportional to $(1/A_D)^2$ and that for $A_D = 0.5$ AU, N = 2850 and at 1.0 AU, N = 711 points for the same conditions used in the baseline calculations above.

N must also be large enough to assure that both sides of a chromatographic peak are included in the average with similar weights. This is so that the errors due to the finite size of the flow cell in combination with the value of d(AU)/dV will be smoothed out and not cause excessive variations in $K_o$. In general, the errors caused by this effect have similar magnitudes and opposite signs on either side of a peak so that the integrated error, over one peak, is approximately zero. Likewise, errors due to less than ideal sweep out characteristics of the flow cells tend to average to zero over an entire peak. Because of these facts, the ideal method would be to average $K_o$ over an entire peak. However, it is not possible to integrate over the entire peak because $A_D$ does not respond above +limit, and for small values of $A_D$ the noise on the calculated ratio becomes too large to be practical Values of $A_D$ between a minimum threshold (typically 0.5 AU for dual beam instrument or lower for a three beam instrument) and the limit determine which portion of a peak is averaged. That is:

$$K_{opeak} = \sum_{t_1,t_3}^{t_2,t_4} K_{o(t)} / \sum_{t_1,t_3}^{t_2,t_4} t$$

$t_1$ = time when $A_{D(t)}$ exceeds threshold on ascending side of peak, $t_2$ = time when $A_{D(t)}$ exceeds +limit on ascending side of peak, $t_3$ = time when $A_{D(t)}$ passes through +limit on descending side of peak, and $t_4$ = time when $A_{D(t)}$ passes through threshold on descending side of peak.

$K_{opeak}$ is calculated once for each peak. The sum of t is simply the number of data points summed and represents the total weight for the peak. If the total peak weight is greater than about 3000 the variance due to noise from the lamp will be less than 0.1% when using a fixed voltage reference on $A_2$. In the DYNAMAX UV-1, $K_o$ is only change at the end of a user definable calibration period or it can be directly changed by the user. A user selects when calibration takes place and the number of chromatographic peaks to be used for determining $K_o$. In this manner, the user can control such parameters as the absorbing compound used, the wavelength monitored, and the volume width of the peaks in order to reduce errors due to non linear response on the long path and the derivative of absorbance versus volume. Reduction of these errors will result in a more accurate $K_o$ determinination. The number of peaks selected together with their width determines the total number of data points averaged and hence the variance of $K_o$ due to noise on the short path signal.

During the calibration period, the current $K_o$ is used to extend the relative absorbance and a bi-polar pulse is superimposed on the output to indicate to the user that the peaks are being used for calibration and the current $K_o$ is in question and will change at the end of the calibration period.

Relative Absorbance Extension

If the extended range mode is turned on and the value of $A_D$ reaches the start blending point (see FIG. 5) a smooth transition is made on the output of the detector from 100% ($A_D$) to 100% ($A_2 * K_o$) when the output reaches +limit and thereon continues to increase as far as the $A_2 * K_o$ signal extends If extended range mode is off, $A_D$ and the output will clip at +limit.

An Alternate Approach For Determining $K_o$

Although the above approach is the one basically followed in the DYNAMAX Model UV-1 Absorbance Detector, it is by no means the only way to deal with the high noise content on the short pathlength signal. Another approach would be to calculate:

$$Error = A_D - A_2 * K_o$$

for every data point. If $K_o$ is the correct value then the calculated Error will have a constant average value (equal to zero if $A_D$ and $A_2$ are properly zero offset). The advantage of this system is that zero offsets do not have to be used because the calculated Error will itself carry the offsets. The resulting Error signal is integrated over two portions. The first portion is the baseline determined by the value of $A_D$ compared to the Baseline Calculate Limit, and the second portion is the peak determined by the value of $A_D$ compared to the Threshold value. The integrated value of these two portions are compared to each other and their difference is used to adjust the value of $K_o$. $K_o$ is adjusted in such a way that it nulls the difference between the two integrated signals to a zero value. If the value of $K_o$ is larger than its true value the integrated peak portion will be smaller than the integrated baseline portion; likewise, if $K_o$ is smaller than its true value the peak portion will be larger than the baseline value. The proper integration time constants can be calculated by analysis similar to the first method described.

Dual Beam Detector of FIG. 3 and Software Routines therefor

Figure 7:
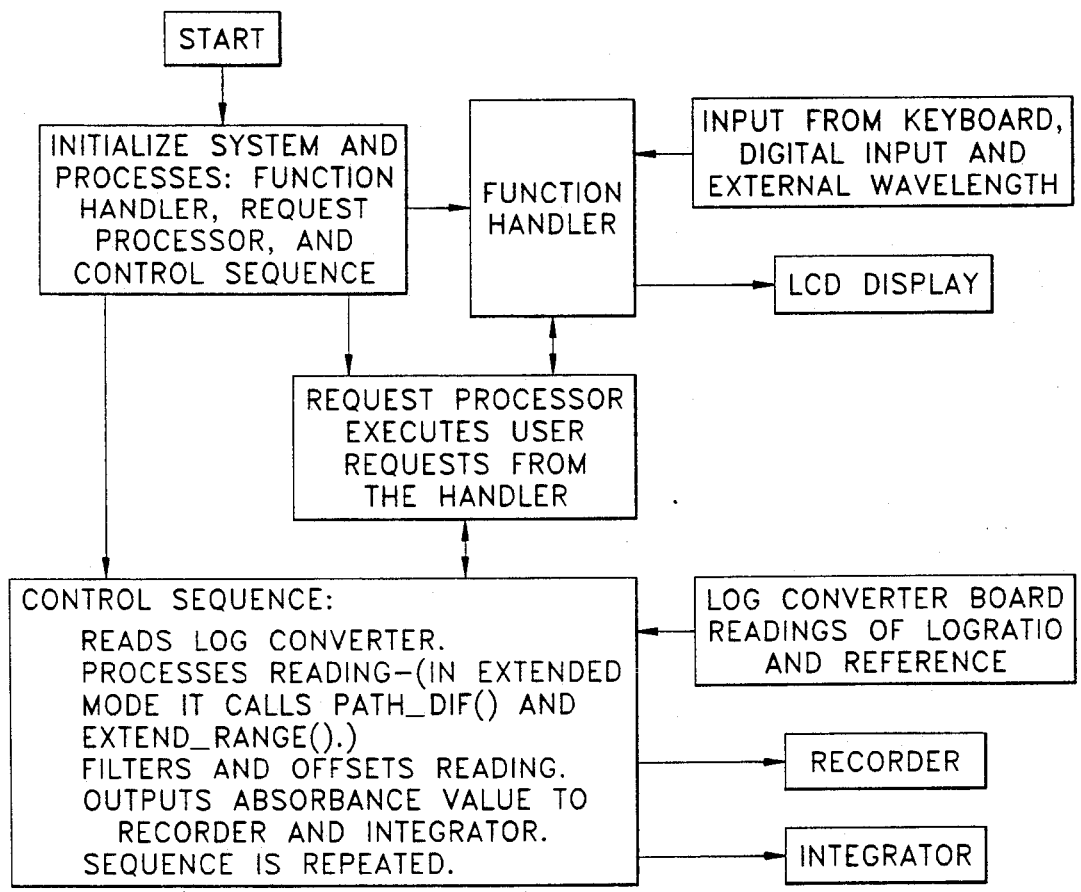
FIG. 7 is a basic flow chart for the software control of the microprocessor of FIG. 3 illustrating the control processing sequence.

When the present invention is implemented in a system which is microprocessor controlled, as in FIG. 3, where the microprocessor (26) preferably comprises a Motorola 68000 general purpose 16-bit microprocessor, the software routines and extended range algorithm are as depicted in FIGS. 7-11. As represented in FIG. 7, the three major processes or tasks of the detector software are embodied in a function handler processor, a request processor and a control sequence processor.

In operation, the detector software in the microprocessor (26) starts when power is turned on. This initializes the detector hardware, the operating system and the three software processors. In this regard, the function handler receives user keyboard inputs, digital inputs and analog external wavelength inputs. The A/D converter (22) converts the analog voltage to a digital signal. The function handler takes the digital signal and converts it to a wavelength. In addition, the function handler reads and interprets all input data, decides what the user is asking, converts what is being asked into a request of the detector and sends requests to the request processor.

The request processor controls the function handler and control sequence processor and executes user requests from the function handler to develop software and hardware control signals for changing wavelength and recorder and integrator range and response times.

The control sequence processor continually repeats the following sequence:
1. Read A/D converter logratio or reference values.
2. Check and convert the logratio and reference values into absorbance values $A_D$ and $A_2$. If the detector system is in its extended range mode, a portion of the process is to execute the following routines on every iteration of the control sequence,
   a. path difference routine, see "path—dif" in FIG. 9,
   b. extend range routine, see "extend—range" in FIG. 9, and
   c. filter reference routine, see "filter—ref" in FIGS. 11a and 11b.

If the detector system is not in the extended range mode, "path—dif" and "filter—ref" are executed at 1 Hz intervals or every other iteration of the control sequence when the sample passageway is approaching saturation.
3. Filter and offset the processed absorbance data.
4. Output the absorbance to the recorder and the integrator.

Figure 9:
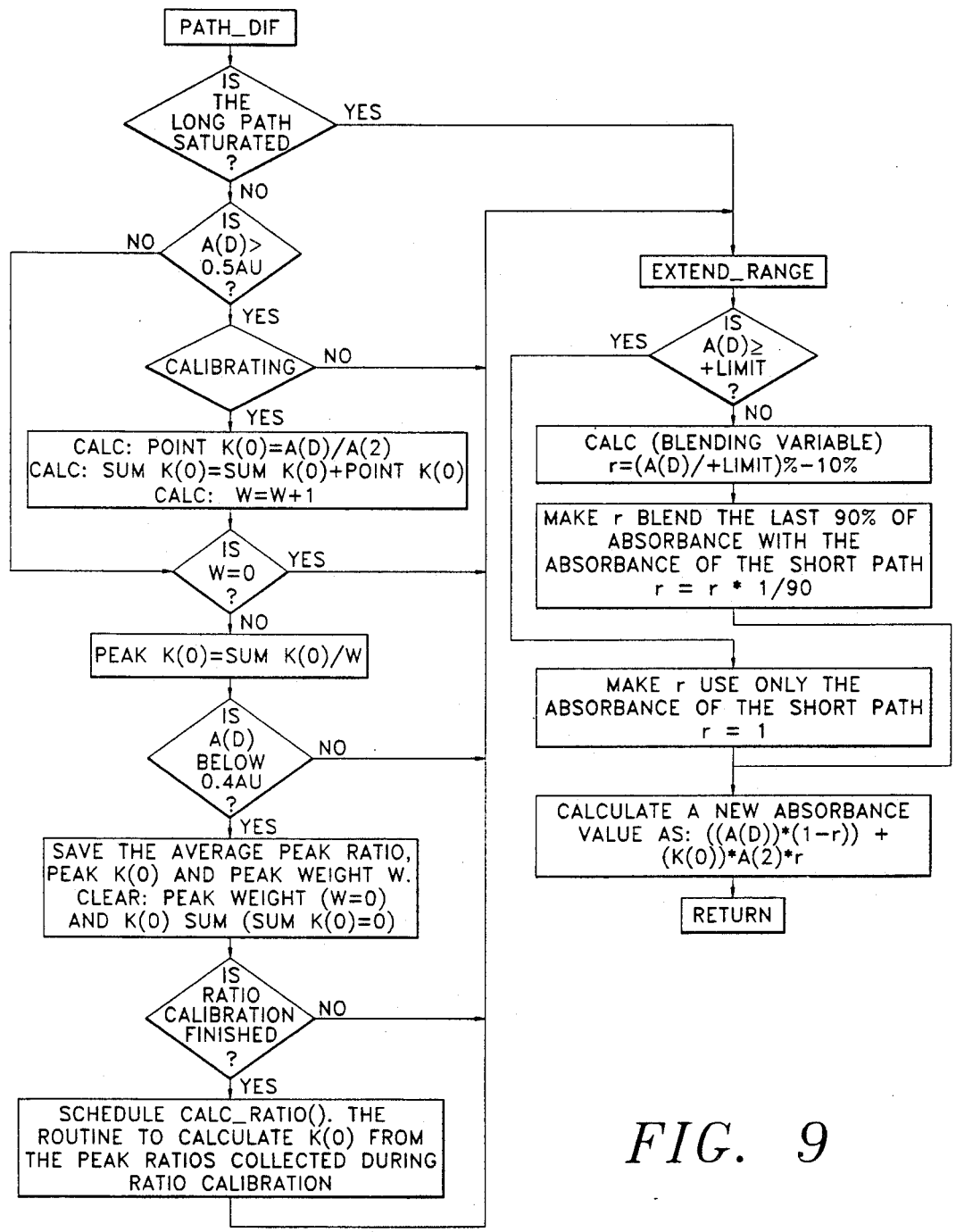
FIG. 9 is a flow chart of the software routines for the calculating of peak path difference ratios and relative absorbance extension of dynamic range in the methods of the present invention.

The extended range algorithm illustrated in FIG. 9 depends upon the use of a path difference flow cell. As previously described, such a cell passes a fluid sample through both a sample and a reference passageway. The extended range algorithm calculates the ratio of the path lengths as sample path length minus reference path length divided by reference path length. The path difference ratio will range from about 1.5 to 30 depending on the design of the flow cell.

Once a path difference ratio is established, it can be used to continue the calculation of a relative absorbance after the sample path saturates by then multiplying the reference path absorbance by the path difference ratio. For optimum response, the extended range routine is used to effect such a calculation of relative absorbance when the recorder output time response is greater than or equal to 1.0 second and the recorder range is greater than or equal to 1.5 AU full scale.

Figure 8:
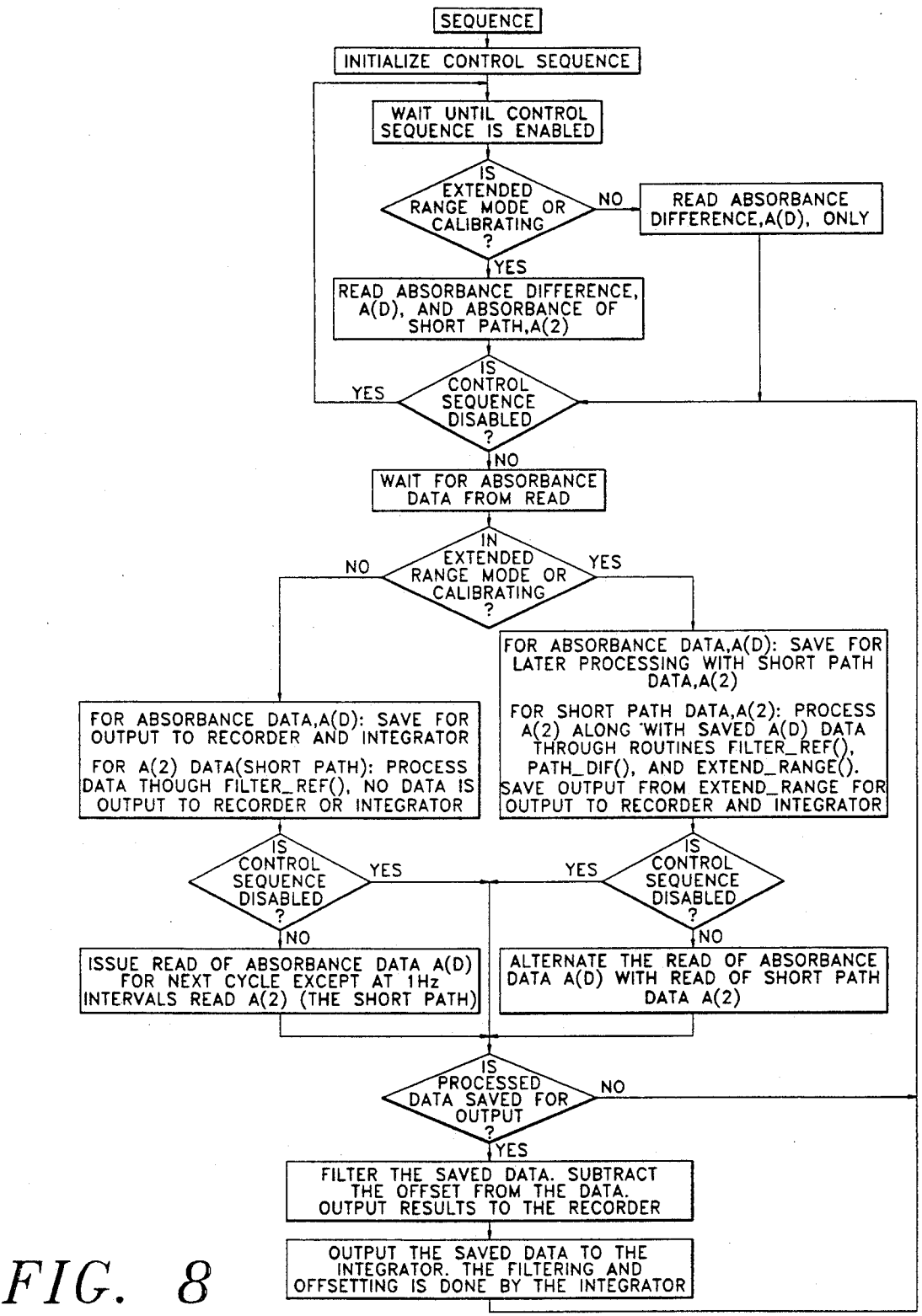
FIG. 8 is a more detailed showing of the control processing sequence of FIG. 7.

While FIG. 7 is a rather general flow chart of the flow processing sequence, FIG. 8 illustrates a more detailed version of the control processing sequence for the FIG. 3 detector system. In the flow chart, A(D) and A(2) are referenced. They are the same as the previously described, $A_D$ (the measured path difference absorbance) and $A_2$ (the measured short path absorbance). The reference routines filter—path, path—dif and extend—range are the routines illustrated in flow chart form in FIGS. 9 and 11a and 11b. The referenced calibrating mode "calc—ratio" in FIG. 9 is the routine illustrated in the flow chart of FIG. 10.

Referring particularly to the flow chart of FIG. 9, the path difference routine is executed whenever a logratio and a reference absorbance reading have been made. Such readings are used to calculate the path difference ratio $K_o$ when a ratio calibration period has been requested by the user. The purpose of the routine is to calculate a path difference ratio for the flow cell used in the detector system for each chromatographic peak occurring during a ratio calibration period. The calculation is executed when the sample path is not saturated and there is an absorbance greater that 0.5 AU. If the sample path is saturated, the routine path—dif provides and indication that saturation has occurred. If the sample path has not reached saturation and there is enough absorbance, the path difference routine calculates the path difference ratio for each data set and sums all such ratio reading over an entire absorbance peak. The number of data sets summed on a given peak is tracked in the parameter W (peak weight). A peak is defined as beginning when the absorbance is equal to or greater than 0.5 AU and as ending when the absorbance falls below 0.4 AU. At the end of a peak, an average ratio is calculated ("peak$K_o$"), and saved in the system along with its weight (W) for further processing to determine $K_o$ at the end of the calibration period.

The extended range routine illustrated in FIG. 9 inputs a logratio reading of the path difference absorbance $A_D$ and the short or reference path absorbance $A_2$. The routine calculates a relative absorbance reading ($A_1'$ previously described) which may be smoothed before the sample path saturates or computed from the short or reference path absorbance only. As illustrated, and as previously described in the Dual Beam Implementation, if $A_D$ is not equal to or greater that its +Limit, the routine calculates a blending or smoothing ratio r which specifies the percentage of the short reference path absorbance $A_2$ to be used in calculating the absorbance $A_1'$. If the path—dif routine has determined that the sample path has saturated, the extended range routine calculates a new absorbance value based upon the short path absorbance only. If sample path saturation has not occurred, the routine will use a portion of $A_D$ and $A_2$ to determine the absorbance output $A_1'$. Preferably, blending is accomplished when $A_D$ is between 10 and 100% of saturation.

Figure 10:
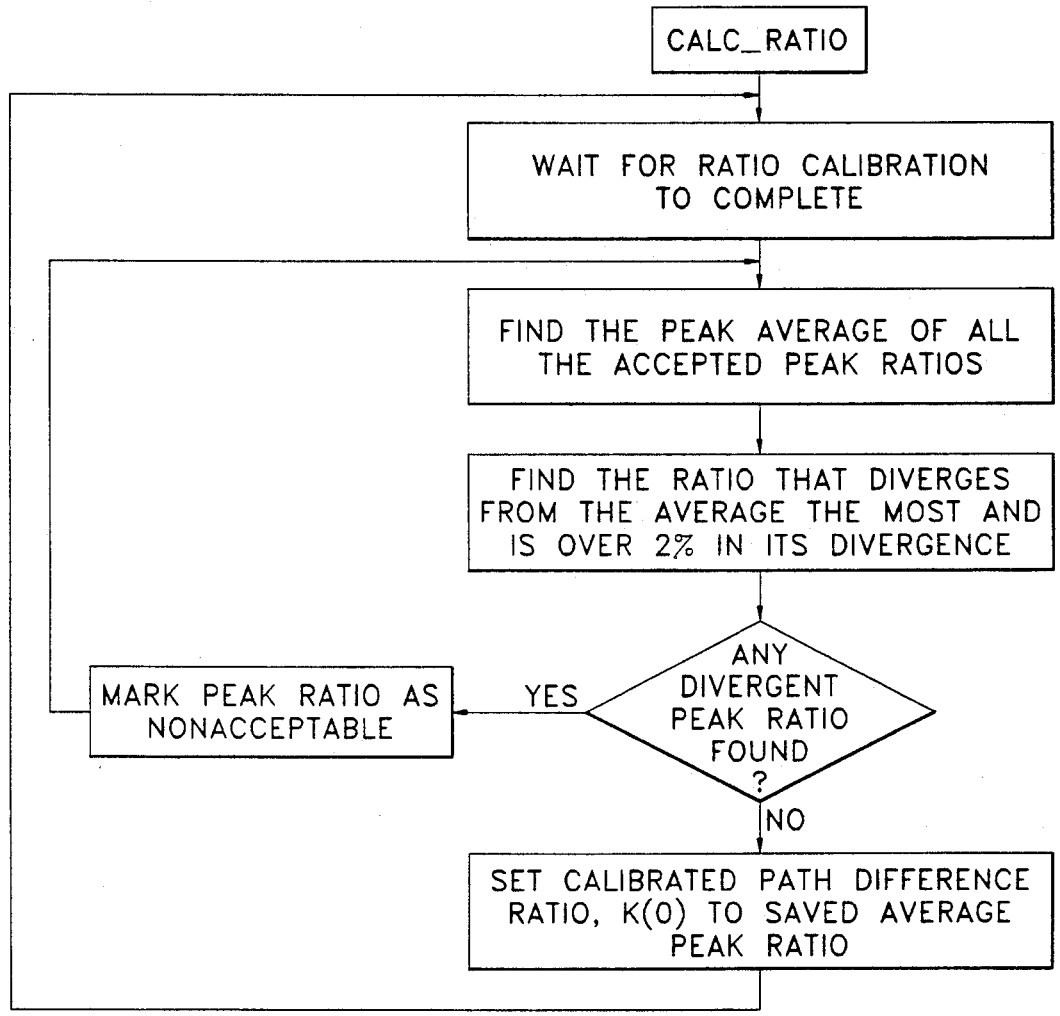
FIG. 10 is a flow chart of the ratio calibration algorithm for the calculation of the peak path difference ratio referenced in FIG. 9.

As previously indicated, FIG. 10 illustrates the ratio calibration algorithm for the calculation of the path difference ratio, $K_o$. As shown in the flow chart of FIG. 9, this routine (calc ratio) is scheduled by the path—dif routine after Ratio Calculation has calculated and saved the required number of peak values which defines the end of the ratio calibration period. The calc—ratio routine waits for the Ratio Calibration to be complete and then finds the peak average of all the accepted peak ratios. From such findings, the routine locates the individual peak ratio that diverges from the average the most and is over 2% in its divergence. Any such divergent peak ratio is marked as unacceptable and $K_o$ is calculated again without the marked peak. The above process is repeated until no such divergent peak ratios are found. The resulting calibrated peak difference ratio $K_o$ is set to the saved average peak ratio and is not changed again until the user decides to repeat the ratio calibration period.

As depicted in the flow chart of FIG. 8 for the control processing sequence, after path difference absorbance $A_d$ and the short path absorbance $A_2$ have been determined, the routine includes the subroutine of filter reference, whether or not the extended range routine is to be executed. The filter reference routine (filter—ref) is as illustrated in the flow charts of FIGS. 11a and 11b.

The filter—ref routine is input absorbance $A_D$, short path absorbance $A_2$ and an extended range mode indicator. The purpose of the routine is to generate a reference path offset. At auto zero, the routine averages the reference path absorbance $A_2$ and filter the value as long as the absorbance is less than 0.01 AU (or 0.1 AU if the path difference ratio $K_o$ is good). More particularly, at autozero, filter—ref averages at most 100 reference data points to generate a new reference offset. This value is flagged as good and is used by path—dif in calculating the path difference ratio. The filter—ref routine continues to filter the reference offset as long as the absorbance is not above 0.01 AU or 0.1 AU if the path difference ratio is accurate.

If a user changes, by keyboard entry, the current wavelength, the reference offset must be recalculated for the new wavelength. The filter—ref routine does this by filtering the reference offset with reference data points for a minimum of 7500 times. Such filtering is accomplished only if the absorbance is below the previously described limits. Until a new reference offset is established for the new wavelength, the flag is set to bad and no ratio calculations are performed in the path—dif routine and no reference data extensions are computed in the extend—range routine.

Figure 11A:
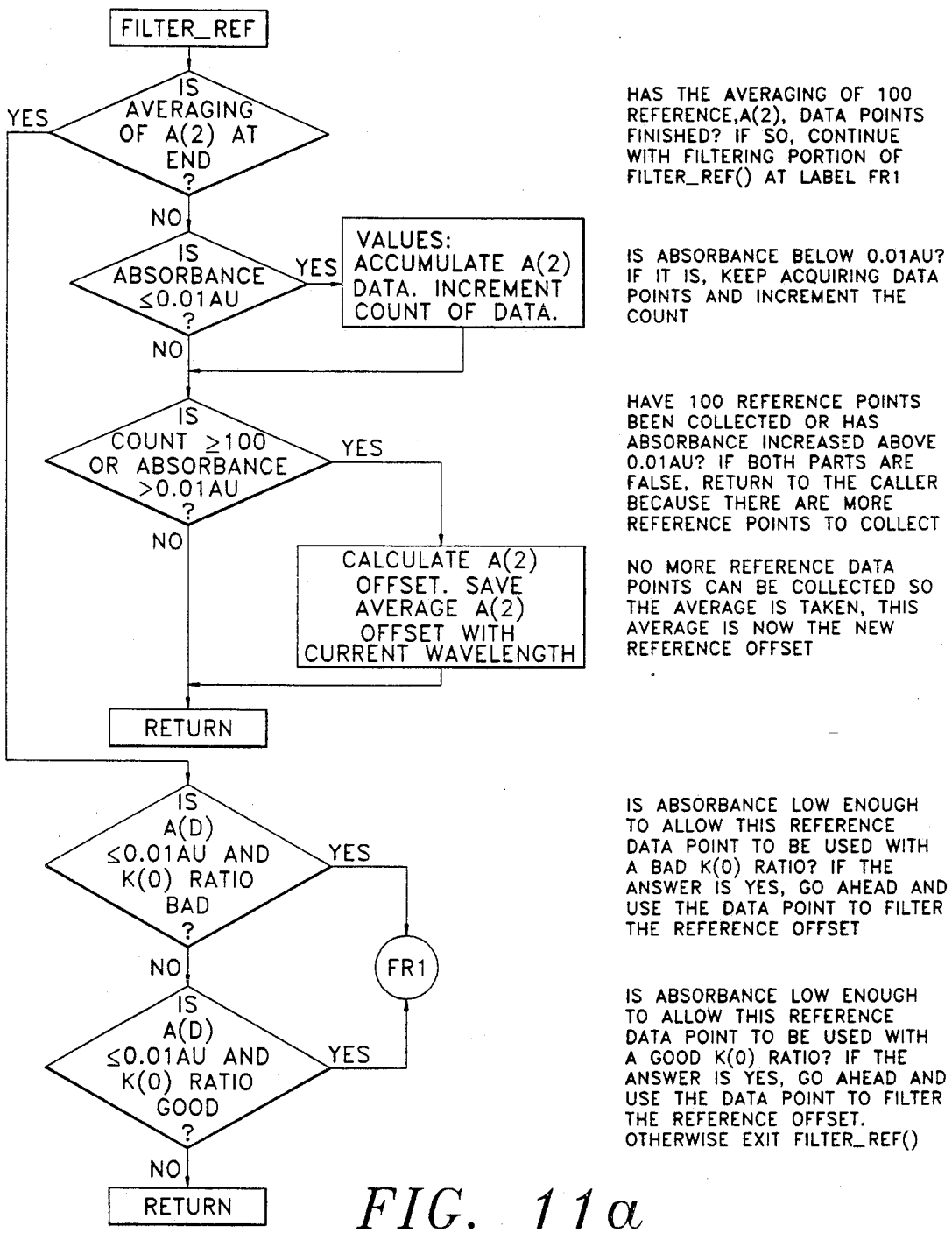
FIGS. 11a and 11b combine to illustrate the flow chart of the software routine filter reference referenced in FIG. 9.
Figure 11B:
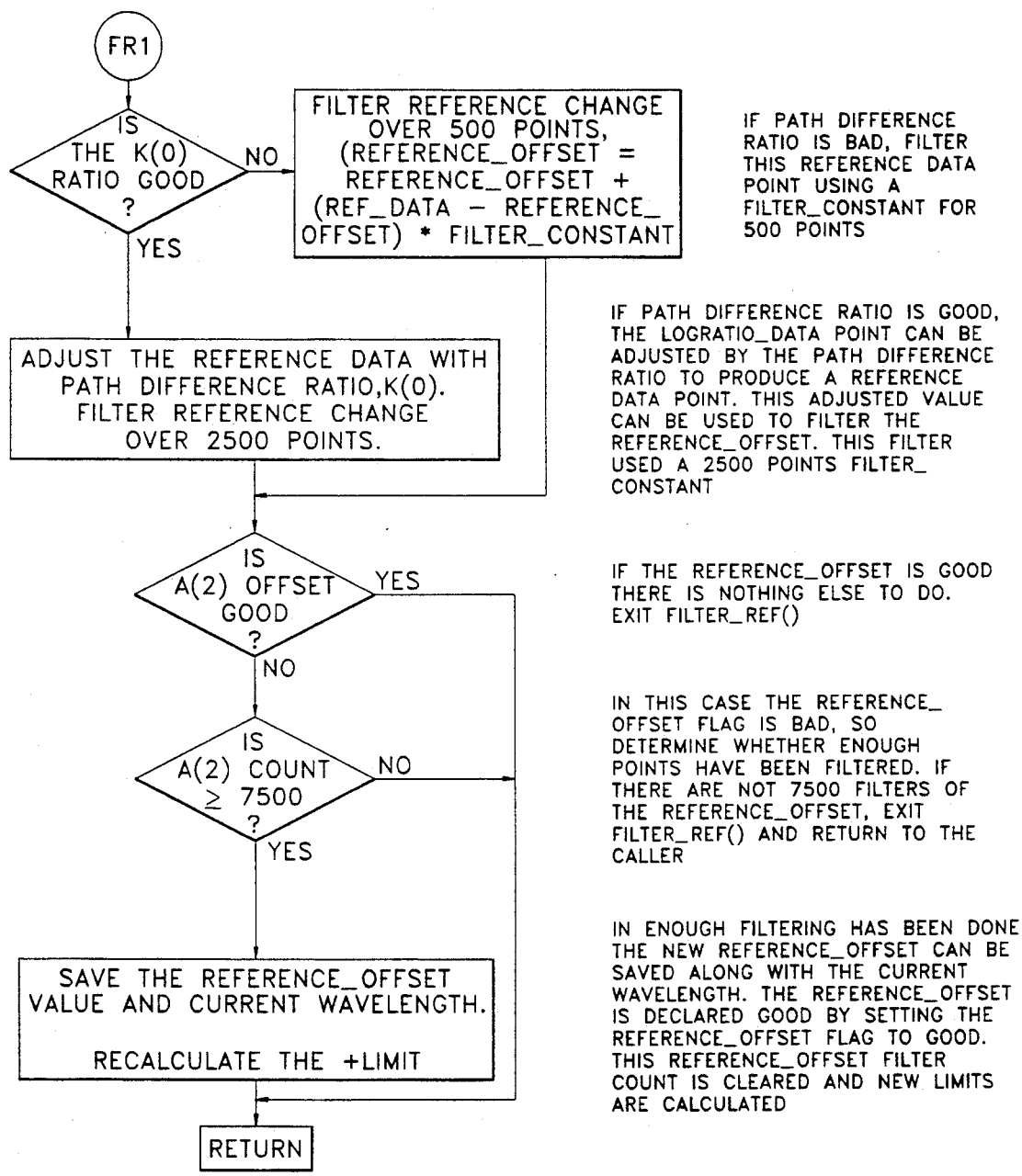

The foregoing is illustrated in the flow chart representation and highlighted in the right column text set forth in FIGS. 11a and 11b and reference should be made to such showings and text for a more complete understanding of the filter reference algorithm.

Triple Beam Implementation of Second Order Extended Range

To apply the second order correction for extended range, the value of $K_A$ must be determined accurately in real time and stored as a function of $A_1$ or $A_D$ for a given peak. The error that results from the change in absorbance as a function of volume (dA/dV) and the finite separation volume between the two different pathlengths must be accounted for and appropriate corrections made. In the dual beam systems shown in FIGS. 1 and 2 the following relationship exists:

$$A_2 *K_A = A_1 + V_d *(dA_1/dV)$$

where:
$V_d$ = the effective delay volume between the two different pathlengths, $$(dA_1/dV) = (dA_1/dt)/f$$

where:
f = the flow rate through the flow cells
Combining the above equations gives:

$$(A_2 *K_A - A_1)/(dA_1/dt) = v_d/f$$

If it is assumed that the flow rate is a constant then $V_d/f$ can be determined when $K_o$ is substituted for $K_A$ and the left hand side of the above equation is averaged over an entire peak. On following peaks, $K_A$ can be calculated real time from the above equation once $V_d/f$ is known from the previous peak (assuming that $A_2$ is a low noise signal). For safer, more fail proof operation the detector should be given the actual flow rate from the system pump.

A preferred method for applying the second order correction to extended range is to use a third pathlength in a third optic beam as illustrated in FIG. 3. A short pathlength functioning as a first short pathlength ($L_3$) is added in series with the first two pathlengths ($L_1$, $L_2$)

on the opposite side of the long pathlength ($L_1$). The following relationships exists:

$$A_2 * K_{A(1,2)} = A_1 + V_{d(1,2)} * (dA_1/dV)$$

$$A_3 * K_{A(1,3)} = A_1 - V_{d(1,3)} * (dA_1/dV)$$

Rearranging:

$$(A_1 - A_2 * K_{A(1,2)})/(dA_1/dV) = -V_{d(1,2)}$$

$$(A_1 - A_3 * K_{A(1,3)})/(dA_1/dV) = V_{d(1,3)}$$

By flow cell construction:

$$V_{d(1,2)} = V_{d(1,3)}$$

Therefore:

$$A_1 - A_2 * K_{A(1,2)} = -A_1 + A_3 * K_{A(1,3)}$$

Or:

$$A_1 = (A_3 * K_{A(1,3)} + A_2 * K_{A(1,2)})/2$$

It can be seen from this last equation that the derivative dA/dV cancels out and does not enter into the extended range calculation when three pathlengths are used as illustrated in FIG. 3. This greatly enhances the accuracy of the extended range calculation and allows for a better second order correction to be made. Since:

$$K_{A(1,2)}/K_{A(1,3)} = K_{o(1,2)}/K_{o(1,3)} = l_3/l_2 = k \text{ (a constant)}$$

$K_{o(1,2)}$, $K_{o(1,3)}$ and k can be determined very accurately with averaged data over many complete peaks. From the above equations the real time $K_{A(1,2)}$ and $K_{A(1,3)}$ can be determined from measured values as follows:

$$K_{A(1,3)} = 2A_1/(A_3 + k * A_2)$$

$$K_{A(1,2)} = 2A_1/(A_2 + A_3/k)$$

The calculated $K_{A(1,2)}$ and $K_{A(1,3)}$ values should be stored in a table along with the associated value of $A_1$ for each ascending side of a peak so that they can be used for calculating the relative absorbance in extended range for the same peak. Extended range relative absorbances with second order correction can be determined with any of the following three equations:

$$A_1 \text{ extended} = K_{o(1,3)}^2 * A_3/K_{A(1,3)}$$

$$A_1 \text{ extended} = K_{o(1,2)}^2 * A_2/K_{A(1,2)}$$

or $$A_1 \text{ extended} = (K_{o(1,3)}^2 * A_3/K_{A(1,3)} + K_{o(1,2)}^2 * A_2/K_{A(1,2)})/2$$

The last equation takes the average of extended relative absorbance from both short pathlengths which, in general, should be more accurate. The average relative absorbance also averages out any time shift between $A_1$ and $A_1$ extended due to $V_d$. The third equation is the preferred equation to use because of its improved accuracy.

Obviously, different variations in the manipulation of the basic absorbance data can be done without departing from the spirit of the above method. For example, $A_{D(1,2)}$ or $A_{D(1,3)}$ can be substituted for $A_1$ with appropriate changes to the above equations without effecting the end result of a second order corrected extended range. Also the three pathlength flow cell can be constructed so that it contains only one short pathlength which is placed between two longer pathlengths as illustrated in FIG. 2.

Triple Pathlength System for Improved Performance in Normal Operation

Figure 12:
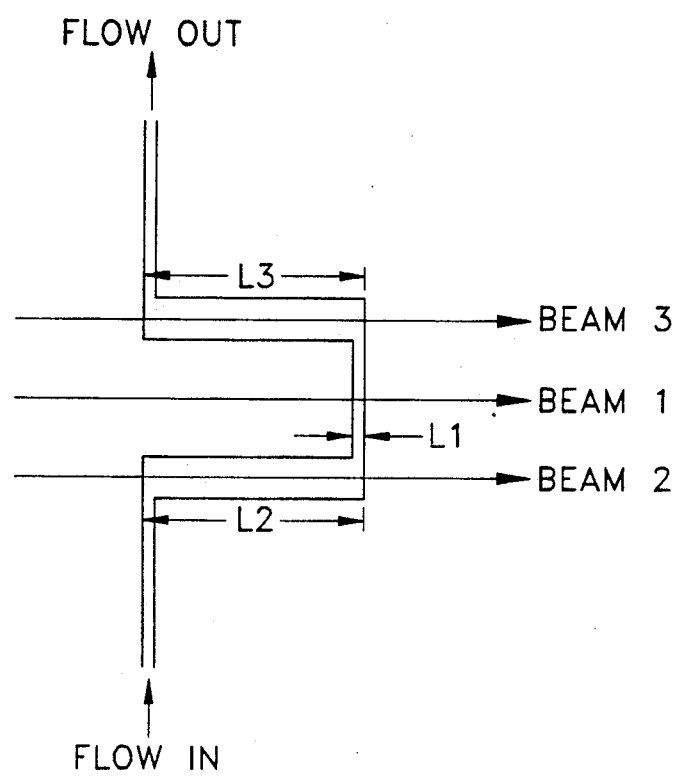
FIG. 12 illustrates a triple beam and pathlength system for improved absorbance detection.

The triple pathlength system described above for second order correction to extended range also has some unique advantages in normal (non extended range) operation when the signals are properly combined. An ideal absorbance detector should not respond to the refractive index (RI) or the derivatives of RI of the sample fluid. Absorbance detectors designed to have low RI sensitivity still have residue sensitivity to RI, especially steep RI gradients or derivatives of RI. The pathdifference absorbance signal from a dual beam, dual pathlength flow cell absorbance detector (described earilier and illustrated in FIG. 2) still has a small residual sensitivity to RI derivatives. The sign of the error due to changes in RI is determined by the direction of flow through the flow cell. Signals from triple pathlength flow cells illustrated in FIG. 3 and FIG. 12 can be processed to further reduce this RI sensitivity. If the pathdifference signals between the middle pathlength and each of the two outer pathlength are calculated it can be seen that the flow through each pathdifference pair is in the opposite sense. Therefore, if the two pathdifference absorbance signals are summed the errors due to RI derivatives with opposite signs will tend to cancel which further minimizes the sensitivity of the instrument to RI changes in the flowing solvent.

We claim:

1. A method of extending the linear dynamic range of an absorbance detector including a multiple light path flow cell having at least a relatively long sample beam passageway and a relatively short reference beam passageway each passing a sample fluid under test and including photo detector means for receiving the sample and reference beams and for developing output signals which are measures of the absorbance of the sample and reference beams in the sample fluid, comprising the steps of:

(1) irradiating the fluid under test in the sample and reference beam passageways with sample and reference light beams, respectively:

(2) detecting the amount of light in the sample beam transmitted through the sample fluid flowing through the sample passageway to determine the absorbance ($A_1$) of the sample beam in passing through the fluid sample in the sample passageway for fluid absorbances within the linear dynamic absorbance range of the sample beam passing through the sample passageway;

(3) detecting the amount of light in the reference beam transmitted through the sample fluid passing through the reference passage way to determine the absorbances ($A_2$ and $A_2'$) of the reference beam in passing through the fluid sample in the reference passageway for fluid sample absorbances respectively within and beyond the linear dynamic absorbance range of the sample beam passing through the sample passageway; and (4) form $A_2'$ developing a linearized relative absorbance ($A_1'$) for the sample beam passing through the sample passageway over fluid sample absorbances beyond the linear dynamic absorbance range of the sample beam passing through the sample passageway.

2. The method of claim 1 wherein step (4) comprises multiplying $A_2'$ by a ratio of $A_1$ to $A_2$.

3. The method of claim 1 wherein step (4) comprises:
determining that the fluid sample absorbance has reached a predetermined percentage of a limit of the linear dynamic absorbance range of the sample beam passing through the sample passageway,
multiply $A_2'$ by a ratio of $a_1$ to $A_2$ to produce $A_1'$ and
upon the fluid sample absorbance reaching the predetermined percentage, blending $A_1$ with $A_1'$ while increasing the contribution of $A_1'$ and simultaneously reducing the contribution of with increasing fluid sample absorbance.

4. The method of claim 1 wherein step (4) comprises multiplying $A_1$ by a ratio determined by a length difference between the sample and reference passageways and the length of the reference passageway $((L_1-L_2)/L_2)$.

5. The method of claim 1 further comprising a step (5 of developing an absorbance difference $A_D$ equal to $A_1$ minus $A_2$ or $A_2'$, and
wherein step (4) comprises multiplying $A_2'$ by a ratio of $A_D$ to $A_2$.

6. The method of claim 5 wherein
step (5) comprises (a) developing $A_D$ for fluid sample absorbances both within and beyond the linear dynamic absorbance range of the reference beam passing through the fluid sample in the reference passageway, and (b) storing in memory ratios ($K_A$) of $A_D$ developed in step (5) (a) to $A_2$ for fluid sample absorbances beyond the linear dynamic absorbance range of the sample beam passing through the sample passageway yet within the linear dynamic absorbance range of the reference beam passing through the reference passageway, and
step (4) comprises multiplying $A_2$ by a ratio ($K_o$) of $A_D$ to $A_2$ for fluid samples absorbances within the linear dynamic absorbance range of the sample beam passing through the sample passageway and multiplying $A_2$ by $K_o^2/K_A$ for fluid sample concentrations therebeyond ($A_1'=K_o^2 A_2/K_A$).

7. The method of claim 6 wherein the flow cell includes three passageways $L_1$, $L_2$, and $L_3$ in fluid series, for passing three light beams 1, 2, and 3 respectively, and wherein
step (5) comprises developing $K_A$ for absorbance differences $A_D$ for beams 1, 2, and 3 passing through the passageways $L_1$, $L_2$, and $L_3$ ($K_{A(1,3)}$ and $K_{A(1,2)}$), and wherein
step (4) comprises developing $A_1'$ by multiplying a square of $K_o$, developed from the absorbances of the passageways $L_1$ and $L_3$ ($K_{o(1,3)}$), by the absorbance of beam 3 in passing through passageway $L_3$ and dividing by $K_A$ for passageways 1 and 3 ($K_{A(1,3)}$).

8. The method of claim 7 wherein
step (4) comprises averaging $A_1'$ developed from $K_{o(1,3)}$ and $A_3$ and $K_{A(1,3)}$ pursuant to claim 17 and $A_1'$ developed in a like manner from $K_{o(1,2)}$, and $K_{A(1,2)}$.

9. The method of claim 8 wherein step (4) comprises adding the absorbance differences $A_D$ for beams 1, 2, and 3 to eliminate the effects of refractive index and refractive index gradients utilizing a three beam flow cell.

10. The method of claim 1 further comprising a step (5) of developing an absorbance difference ($A_D$) equal to $A_1$ minus $A_2$ or $A_2'$, and
wherein step (4) comprises
determining that the fluid sample absorbance has reached a predetermined percentage of a limit of the linear dynamic absorbance range of the sample passageway, and
multiplying $A_2'$ by a ratio of $A_D$ to $A_2$ to produce $A_D'$, and
upon the fluid sample absorbance reaching the predetermined percentage, blending $A_D$ with $A_D'$ while increasing the contribution of $A_D'$ and simultaniously reducing the contribution of $A_D$ with increasing fluid sample absorbance.

11. The method of claim 1 further comprising a step (6) of determining the absorbance of the sample beam in passing through the fluid sample in the sample passageway for fluid absorbances beyond the linear dynamic absorbance range of the sample beam passing through the fluid sample in the sample passageway yet within a linear dynamic absorbance range of the reference beam in passing through the fluid sample in the reference passageway, and
wherein step (4) comprises developing from the absorbances of steps (3) and (6) the linearized relative absorbance $A_1'$.

12. The method of claim 11 wherein
step (4) comprises developing $A_1'$ from $a_2'$ for fluid sample absorbances beyond the linear dynamic absorbance range of the sample beam passing through the fluid sample in the sample passageway yet within the linear dynamic absorbance range of the reference beam in passing the fluid sample in the reference passageway and developing $A_1'$ from the absorbances determined by step (5) for fluid sample absorbances beyond the linear dynamic absorbance range of the reference beam passing through the fluid sample in the reference passageway.

13. An absorbance detector including a multiple light path flow cell having at least a relatively long sample beam passageway and a relatively short reference beam passageway each passing fluid under test, comprising:
(1) means for irradiating the fluid under test in the sample and reference passageways with sample and reference light beams;
(2) photo detector means for detecting sample and reference light beams passing from the sample and reference passageways to develop first and second output signals which are measures of the absorbance of the sample and reference beams in the sample fluid; and
(3) signal processing means responsive to the first and second output signals for (i) determining absorbances ($A_1$ and $A_2$ ) of the sample and reference beams in passing through the fluid sample in the sample and reference passageways respectively for fluid absorbances within the linear dynamic absorbance range of the sample beam passing through the sample passageway, (ii) determining absorbance ($A_2'$) of the reference beam in passing through the fluid sample in the reference passageway for fluid sample absorbances beyond the linear dynamic absorbance range of the sample beam passing through the sample passageway and (iii) developing from $A_2'$ a linearized relative absorbance ($A_1'$) for the sample beam passing through the sample passageway over fluid sample absorbances beyond the linear dynamic absorbance range of the sample beam passing through the sample passageway.

14. The absorbance detector of claim 13 wherein said signal processing means comprises means for multiplying $A_2'$ by a ratio ($K_o$) of $A_1$ to $A_2$.

15. The absorbance detector of claim 13 wherein said signal processing means comprises:
    means for determining that the fluid sample absorbance has reached a predetermined percentage of a limit of the linear dynamic absorbance range of the sample beam passing through the sample passageway, and
    means for multiplying $A_2'$ by a ratio ($K_o$) of $A_1$ to $A_2$ and upon the fluid sample absorbance reaching the predetermined percentage, blending $A_1$ with $A_1'$ while increasing the contribution of $A_1'$ and simultaneously reducing the contribution of $A_1$ with increasing fluid sample absorbance.

16. The absorbance detector of claim 13 wherein said signal processing means comprises means for multiplying $A_2$ by a ratio determined by a length difference between the sample and reference passageways and the length of the reference passageway (($L_1-L_2$)/$L_2$).

17. The absorbance detector of claim 13 further including
    (4) means for developing an absorbance difference $A_D$ equal to $A_1$ minus $A_2$ or $A_2'$, and wherein
    said signal processing means comprises means for multiplying $A_2'$ by a ratio of $A_D$ to $A_2$.

18. The absorbance detector of claim 13 further comprising
    (4) means for developing an absorbance difference $A_D$ equal to $A_1$ minus $A_2$ or $A_2'$, and wherein
    said signal processing means comprises
    means for determining that the fluid sample absorbance has reached a predetermined percentage of a limit of the linear dynamic absorbance range of the sample beam passing through the sample passageway, and
    means for multiplying $A_2$ by a ratio of $A_D$ to $A_2$ to produce $A_D'$ and upon the fluid sample absorbance reaching the predetermined percentage, blending $A_D$ with $A_D'$ while increasing the contribution of $A_D'$ and simultaneously reducing the contribution of $A_D$ with increasing fluid sample absorbance.

* * * * *